(12) United States Patent
Woo et al.

(10) Patent No.: US 8,629,092 B2
(45) Date of Patent: Jan. 14, 2014

(54) HARD SURFACE CLEANING COMPOSITION HAVING A MALODOR CONTROL COMPONENT AND METHODS OF CLEANING HARD SURFACES

(75) Inventors: Ricky Ah-Man Woo, Hamilton, OH (US); Steven Anthony Horenziak, Cincinnati, OH (US); Rhonda Jean Jackson, Cincinnati, OH (US); Zaiyou Liu, West Chester, OH (US); Michael-Vincent Nario Malanyaon, Indian Springs, OH (US); Jason John Olchovy, West Chester, OH (US); Christine Marie Readnour, Fort Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 449 days.

(21) Appl. No.: 12/969,654

(22) Filed: Dec. 16, 2010

(65) Prior Publication Data

US 2011/0146725 A1 Jun. 23, 2011

Related U.S. Application Data

(60) Provisional application No. 61/287,348, filed on Dec. 17, 2009, provisional application No. 61/287,369, filed on Dec. 17, 2009, provisional application No. 61/287,383, filed on Dec. 17, 2009.

(51) Int. Cl.
 *C11D 3/50* (2006.01)
 *C11D 3/60* (2006.01)
 *C11D 3/00* (2006.01)

(52) U.S. Cl.
 CPC .................................. *C11D 3/0068* (2013.01)

USPC ............................................ 510/101; 510/405

(58) Field of Classification Search
 USPC .................................................. 510/101, 405
 See application file for complete search history.

(56) References Cited

U.S. PATENT DOCUMENTS

| | | | |
|---|---|---|---|
| 5,942,217 A | 8/1999 | Woo et al. | |
| 5,955,093 A | 9/1999 | Woo et al. | |
| 6,033,679 A | 3/2000 | Woo et al. | |
| 6,306,812 B1 | 10/2001 | Perkins et al. | |
| 6,537,957 B1 * | 3/2003 | Rescio et al. | 510/238 |
| 6,740,713 B1 * | 5/2004 | Busch et al. | 525/417 |
| 6,753,305 B2 * | 6/2004 | Raso et al. | 510/438 |
| 6,972,276 B1 * | 12/2005 | Besselievre et al. | 510/101 |
| 7,135,449 B2 | 11/2006 | Li et al. | |
| 7,169,741 B2 | 1/2007 | Barry et al. | |

(Continued)

FOREIGN PATENT DOCUMENTS

| | | |
|---|---|---|
| EP | 2008637 A1 | 12/2008 |
| WO | WO 02/092746 A1 | 11/2002 |
| WO | WO 2008/059189 A1 | 5/2008 |

OTHER PUBLICATIONS

International Search Report dated Feb. 11, 2011 containing 197 pages.

*Primary Examiner* — Gregory Webb
(74) *Attorney, Agent, or Firm* — John T. Dipre; Amy I. Ahn-Roll

(57) ABSTRACT

A hard surface cleaning composition comprising a malodor control component, and methods of cleaning hard surfaces are provided. In some embodiments, the hard surface cleaning composition comprises at least one volatile aldehyde and an acid catalyst.

26 Claims, 1 Drawing Sheet

(56) References Cited

U.S. PATENT DOCUMENTS

| | | |
|---|---|---|
| 7,199,093 B2 | 4/2007 | Li et al. |
| 7,393,521 B2 | 7/2008 | Hruza |
| 7,425,526 B2 | 9/2008 | Li et al. |
| 7,470,652 B2 * | 12/2008 | Kilkenny et al. ............ 510/191 |
| 8,357,359 B2 * | 1/2013 | Woo et al. .................. 424/76.2 |
| 8,440,604 B2 * | 5/2013 | Barger et al. ............... 510/397 |
| 8,461,089 B2 * | 6/2013 | Woo et al. .................. 510/101 |
| 2003/0158079 A1 | 8/2003 | Dykstra et al. |
| 2004/0018955 A1 | 1/2004 | Wevers et al. |
| 2004/0106528 A1 | 6/2004 | Bettiol et al. |
| 2004/0144406 A1 * | 7/2004 | Garabedian et al. .......... 134/26 |
| 2005/0245424 A1 * | 11/2005 | Patel et al. ................ 510/439 |
| 2006/0128585 A1 * | 6/2006 | Adair et al. ............... 510/383 |
| 2006/0287219 A1 * | 12/2006 | Dykstra et al. ................ 512/10 |
| 2007/0294328 A1 | 12/2007 | Schneiderman et al. |
| 2008/0032910 A1 * | 2/2008 | Smets et al. ................ 510/342 |
| 2008/0194454 A1 | 8/2008 | Morgan et al. |
| 2010/0111889 A1 * | 5/2010 | Marsh et al. ............... 424/76.1 |
| 2010/0113616 A1 * | 5/2010 | Gerke et al. ............... 514/769 |
| 2011/0146001 A1 * | 6/2011 | Woo et al. .................... 8/137 |
| 2011/0146725 A1 * | 6/2011 | Woo et al. .................... 134/26 |
| 2011/0150814 A1 * | 6/2011 | Woo et al. .................. 424/76.2 |
| 2011/0150815 A1 * | 6/2011 | Woo et al. .................. 424/76.2 |
| 2011/0150816 A1 * | 6/2011 | Woo et al. .................. 424/76.2 |
| 2011/0150817 A1 * | 6/2011 | Woo et al. ................. 424/76.21 |
| 2011/0152157 A1 * | 6/2011 | Woo et al. .................. 510/236 |
| 2011/0152804 A1 * | 6/2011 | Woo et al. .................. 604/359 |
| 2011/0305659 A1 * | 12/2011 | Woo et al. ................. 424/76.21 |

* cited by examiner

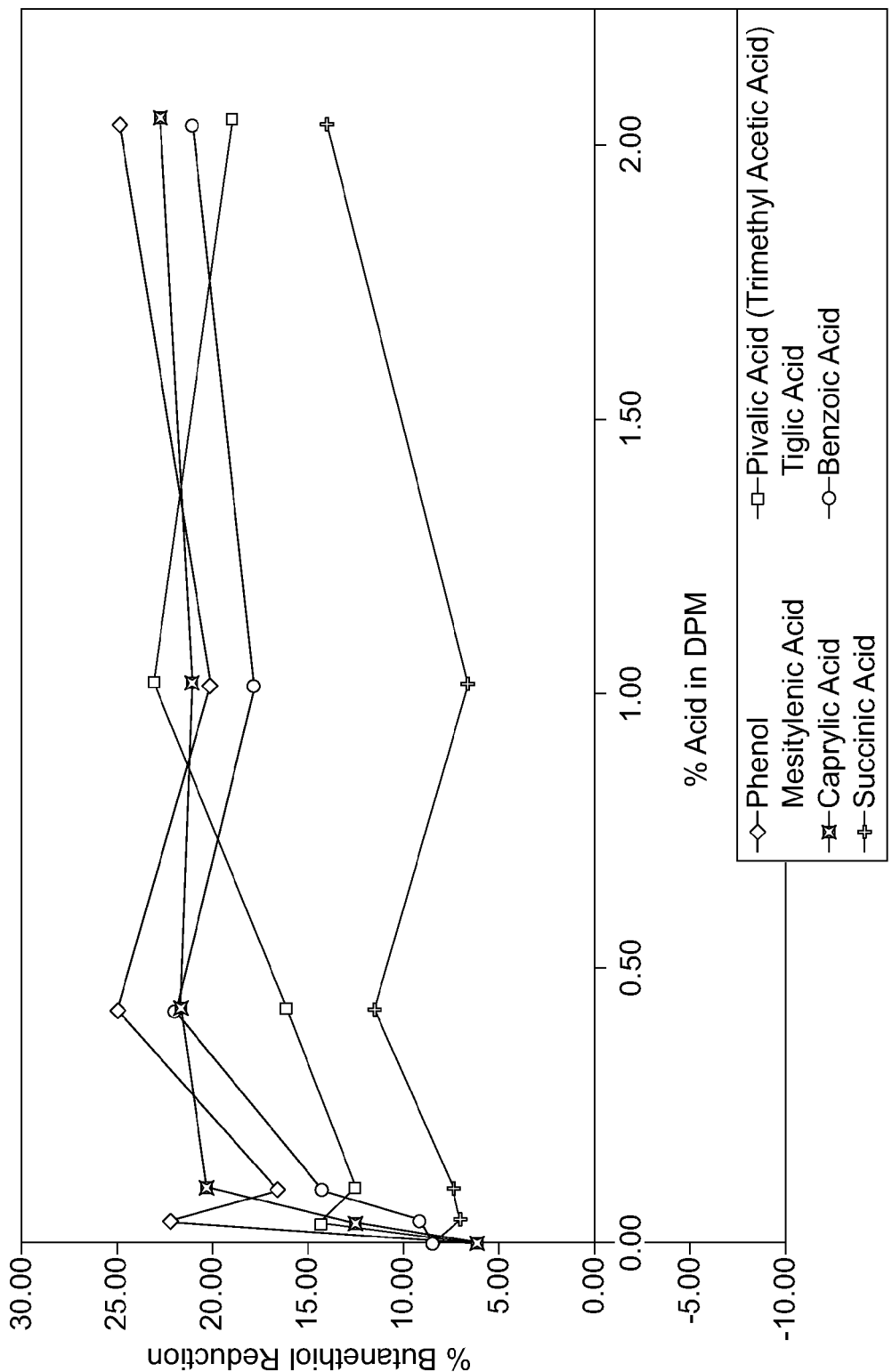

HARD SURFACE CLEANING COMPOSITION HAVING A MALODOR CONTROL COMPONENT AND METHODS OF CLEANING HARD SURFACES

CROSS REFERENCE TO RELATED APPLICATIONS

This application claims the benefit of U.S. Provisional Application No. 61/287,348, filed Dec. 17, 2009 and U.S. Provisional Application No. 61/287,369, filed Dec. 17, 2009 and U.S. Provisional No. 61/287,383, filed Dec. 17, 2009.

FIELD OF THE INVENTION

The present invention relates to hard surface cleaning compositions having a malodor control component, and methods for cleaning hard surfaces.

BACKGROUND OF THE INVENTION

Scented hard surface cleaning compositions are known. Typically, hard surface cleaning manufacturers develop perfume technology that provides a pleasant scent and masks malodors associated with soiled hard surfaces.

However, not all odors on hard surfaces are effectively controlled by products on the market because amine-based malodors such as fish and urine malodors, and sulfur-based malodors such as garlic, onion, foot, and fecal malodors are difficult to combat. Further, the time required for a product to noticeably combat malodors may create consumer doubt as to a product's efficacy on malodors. For example, the consumer may finish cleaning a hard surface and leave the area before the product begins to noticeably reduce the malodor.

The difficulty in overcoming a broad range of malodors has spawned a diverse assortment of products to neutralize, mask, or contain the malodors. There remains a need for a hard surface cleaning composition that cleans and is effective on a broad range of malodors, including amine-based and sulfur-based malodors, while not overpowering malodors with an overwhelming perfume.

SUMMARY OF THE INVENTION

In one embodiment, there is provided a hard surface cleaning composition comprising: (a) an acidic component; (b) a surfactant selected from the group consisting of nonionic surfactants, anionic surfactants, cationic surfactants; amphoteric surfactants, zwitterionic surfactants, and mixtures thereof; and (c) a surface modifying polymer; (d) a malodor control component comprising an effective amount of two or more volatile aldehydes for neutralizing a malodor, wherein said two or more volatile aldehydes are selected from the group consisting of 2-ethoxy benzylaldehyde, 2-isopropyl-5-methyl-2-hexenal, 5-methyl furfural, 5-methyl-thiophene-carboxaldehyde, adoxal, p-anisaldehyde, benzylaldehyde, bourgenal, cinnamic aldehyde, cymal, decyl aldehyde, floral super, florhydral, helional, lauric aldehyde, ligustral, lyral, melonal, o-anisaldehyde, pino acetaldehyde, P.T. bucinal, thiophene carboxaldehyde, trans-4-decenal, trans trans 2,4-nonadienal, undecyl aldehyde, and mixtures thereof; and (e) an aqueous carrier.

In another embodiment, there is provided a hard surface cleaning composition comprising: (a) an acidic mixture comprising formic acid and citric acid; (b) a surface modifying polymer selected from the group consisting of: vinylpyrrolidone homopolymer or copolymer; polysaccharide polymer, and mixtures thereof; and (c) a malodor control component comprising: (i) at least one volatile aldehyde; and (ii) an acid catalyst having a vapor pressure of about 0.01 to about 13 at 25° C.

In yet another embodiment, there is provided a method of cleaning a hard surface or an object, comprising the steps of: applying the hard surface cleaning composition of claim 1 onto said hard-surface or said object; leaving said composition on said hard-surface or said object to act; optionally, wiping said hard-surface or object; and rinsing said hard-surface or said object.

BRIEF DESCRIPTION OF THE DRAWINGS

FIG. 1 is a graph showing butanethiol reduction by thiophene carboxaldehyde in combination with various acid catalysts.

DETAILED DESCRIPTION OF THE INVENTION

The present invention relates to a hard surface cleaning composition for cleaning a variety of hard surfaces including those found in bathrooms, garages, driveways, basements, gardens, kitchens, etc. More specifically, the compositions of the present invention deliver good malodor reduction and limescale removal performance (i.e., removal of pure limescale deposits and/or limescale-containing soils) whilst not being considered corrosive. The present invention also relates to methods of cleaning hard surfaces.

I. Hard Surface Cleaning Composition

The compositions of the present invention are liquid compositions (including gels) as opposed to a solid or a gas. The compositions of the present invention may have a pH of above 2.0, alternatively from 2.0 to 4.0, alternatively from 2.5 to 4.0, alternatively from 3.0 to 3.9, alternatively from 3.0 to 3.6, alternatively from 2.0 to 3.6, alternatively from 2.1 to 3.6, alternatively from 2.1 to 2.9, alternatively from 2.1 to 2.4, alternatively from 2.2 to 2.4. Alternatively, the pH of the cleaning compositions herein, as is measured at 25° C., may be at least 2.0. The pH of the cleaning compositions herein, as is measured at 25° C. may be less than 3.6. In one embodiment, the compositions of the present invention are acidic and have a pH of above 2.0.

In one embodiment, the compositions herein may have a water-like viscosity. By "water-like viscosity" it is meant herein a viscosity that is close to that of water. Alternatively, the liquid acidic hard surface cleaning compositions herein have a viscosity of up to 50 cps at 60 rpm, alternatively from 0 cps to 30 cps, alternatively from 0 cps to 20 cps, alternatively from 0 cps to 10 cps at 60 rpm$^1$ and 20° C. when measured with a Brookfield digital viscometer model DV II, with spindle 2.

In another embodiment, the compositions herein are thickened compositions. Thus, the hard surface cleaning compositions herein alternatively have a viscosity of from 50 cps to 5000 cps at 20 s$^{-1}$, alternatively from 50 cps to 2000 cps, alternatively from 50 cps to 1000 cps and alternatively from 50 cps to 500 cps at 20 s$^{-1}$ and 20° C. when measured with a Rheometer, model AR 1000 (Supplied by TA Instruments) with a 4 cm conic spindle in stainless steel, 2° angle (linear increment from 0.1 to 100 sec$^{-1}$ in max. 8 minutes). Alternatively, the thickened compositions of this specific embodiment are shear-thinning compositions. The thickened hard surface cleaning compositions herein alternatively comprise a thickener, alternatively a polysaccharide polymer (as described herein below) as thickener, still alternatively a gum-type polysaccharide polymer thickener and alternatively Xanthan gum.

The compositions of the present invention may comprise from 70% to 99%, by weight of the total composition, of water, alternatively from 75% to 95%, alternatively from 80% to 95%, and other essential and optional compositions components are dissolved, dispersed or suspended in water.

A. Acidic Component

The compositions of the present invention may include formic acid. Formic acid has been found to provide excellent limescale removal performance. Formic acid is commercially available from Aldrich.

The compositions of the present invention may comprise from 0.01% to 5%, alternatively from 0.5% to 4%, alternatively from 1% to 3%, by weight of the total composition of formic acid.

The compositions of the present invention may comprise citric acid. Suitable citric acid is commercially available from Aldrich, ICI or BASF.

The compositions of the present invention may comprise from 0.1 to 12%, alternatively from 1% to 10%, alternatively from 1.5% to 8%, alternatively from 1.5% to 5% by weight of the total composition of citric acid.

The Applicant has unexpectedly found that by using a formic acid and citric acid-containing composition having a pH of above 2.0, the acidic composition provides good cleaning performance whilst not being corrosive. Indeed, a similar composition having a pH below 2.0 (i.e., un-buffered or not sufficiently buffered) will be corrosive. Indeed, the combination of acids along with the selected pH provides an optimal combination of limescale removal and non-corrosiveness is achieved.

By "corrosive" it is meant herein that the composition has to be labeled as corrosive by means of appropriate text and/or pictograms under the Directive 1999/45/EC of the European Parliament and of the Council of 31 May 1999 concerning the approximation of the laws, regulations and administrative provisions of the Member States relating to the classification, packaging and labelling of dangerous preparations. By "non-corrosive" or "not being/considered corrosive" or the like it is meant herein that the composition has not to be labeled as corrosive by means of appropriate text and/or pictograms under the above Directive.

Indeed, it has been found that hard surface cleaning compositions comprising formic acid and citric acid and having a pH of above 2.0 (alternatively 2.01-3.6), provide a similar or even improved limescale removal performance (i.e., limescale deposits cleaning performance and limescale-containing soil cleaning performance), as compared to the limescale removal performance obtained by a similar composition having a similar pH as claimed herein but comprising formic acid or citric acid on their own or other compositions having a lower pH as claimed herein and comprising formic acid or citric acid in combination with another acid (such as sulfuric acid), at comparable levels of free-acidity.

Furthermore, hard surface cleaning compositions having a pH of above 2.0 and comprising formic acid and citric acid as claimed herein, are not considered corrosive.

The present invention also encompasses the use, in a liquid acidic hard surface cleaning composition, of formic acid, citric acid and an alkaline material, at a pH of above 2.0, to provide limescale removal performance, whilst not being corrosive.

The composition of the present invention may also include other acids, alternatively acetic acid and/or oxalic acid and/or lactic acid.

It has been found that the presence of lactic acid additionally provides antimicrobial/disinfecting benefits to the compositions of the present invention. Lactic acid is commercially available from Aldrich or Purac.

The compositions of the present invention may comprise from 0.1 to 1%, alternatively from 0.1% to 0.75% by weight of the composition of lactic acid.

The compositions herein may comprise acetic acid. Suitable acetic acid is commercially available from Aldrich, ICI or BASF.

The compositions of the present invention may comprise from 0.1 to 1%, alternatively from 0.1% to 0.75% by weight of the composition of acetic acid.

The compositions herein may comprise oxalic acid. Suitable oxalic acid is commercially available from Aldrich or Clariant.

The compositions of the present invention may comprise from 0.1 to 1%, alternatively from 0.1% to 0.75% by weight of the composition of oxalic acid.

B. Alkaline Component

The compositions herein comprise an alkaline material. Indeed, an alkaline material may be present to trim the pH and/or maintain the pH of the compositions of the present invention. Examples of alkaline material are sodium hydroxide, potassium hydroxide and/or lithium hydroxide, and/or the alkali metal oxides such, as sodium and/or potassium oxide or mixtures thereof and/or monoethanolamine and/or triethanolamine. Other suitable bases include ammonia, ammonium carbonate, choline base, etc. In one embodiment, the source of alkalinity is sodium hydroxide or potassium hydroxide, alternatively sodium hydroxide.

Typically the amount of alkaline material is of from 0.001% to 20%, alternatively from 0.01% to 10% and alternatively from 0.05% to 3%, by weight of the composition.

Despite the presence of alkaline material, if any, the compositions herein may remain acidic compositions.

C. Chelating Agent

The compositions of the present invention may comprise a chelating agent or mixtures thereof. Chelating agents can be incorporated in the compositions herein in amounts ranging from 0% to 10% by weight of the total composition, alternatively 0.01% to 5.0%, alternatively 0.05% to 1%.

Suitable phosphonate chelating agents to be used herein may include alkali metal ethane 1-hydroxy diphosphonates (HEDP), alkylene poly(alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities.

Suitable chelating agents to be used herein are diethylene triamine penta methylene phosphonate (DTPMP) and ethane 1-hydroxy diphosphonate (HEDP). In one execution of the present invention, the chelating agent is selected to be ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Suitable compounds of this type in acid form are dihydroxydisulfobenzenes such as 1,2-dihydroxy-3,5-disulfobenzene.

One biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates to be used herein include ethylene diamine tetra acetates, diethylene triamine pentaacetates, diethylene triamine pentaacetate (DTPA), N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents to be used herein include salicylic acid, aspartic acid, glutamic acid, glycine, malonic acid or mixtures thereof.

It has been surprisingly found that the addition of a chelating agent, alternatively HEDP, in the composition of the present invention provides an unexpected improvement in terms of limescale removal.

D. Surfactants

The compositions of the present invention may comprise a nonionic surfactant, or a mixture thereof and/or an anionic surfactant or a mixture thereof. In one embodiment, the compositions of the present invention, comprise a mixture of a nonionic surfactant or a mixture thereof and an anionic surfactant or a mixture thereof. Indeed, it has been surprisingly found that such a mixture contributes to the limescale and greasy soap scum removal performance of the compositions herein.

The compositions of the present invention may comprise a nonionic surfactant, or a mixture thereof. This class of surfactants may be desired as it further contributes to cleaning performance of the hard surface cleaning compositions herein. It has been found in particular that nonionic surfactants strongly contribute in achieving highly improved performance on greasy soap scum removal, the benefit is especially observed at a pH above 3.0.

The compositions of the present invention may comprise up to 15% by weight of the total composition of a nonionic surfactant or a mixture thereof, alternatively from 0.1% to 15%, alternatively from 1% to 10%, even alternatively from 1% to 5%, and alternatively from 1% to 3%.

Suitable nonionic surfactants for use herein are alkoxylated alcohol nonionic surfactants, which can be readily made by condensation processes which are well-known in the art. However, a great variety of such alkoxylated alcohols, especially ethoxylated and/or propoxylated alcohols, is conveniently commercially available. Surfactants catalogs are available which list a number of surfactants, including nonionics.

Accordingly, suitable alkoxylated alcohols for use herein are nonionic surfactants of the formula RO(E)e(P)pH where R is a hydrocarbon chain of from 2 to 24 carbon atoms, E is ethylene oxide and P is propylene oxide, and e and p which represent the average degree of, respectively ethoxylation and propoxylation, are of from 0 to 24 (with the sum of e+p being at least 1). Alternatively, the hydrophobic moiety of the nonionic compound can be a primary or secondary, straight or branched alcohol having from 8 to 24 carbon atoms.

Suitable nonionic surfactants for use in the compositions of the invention are the condensation products of ethylene oxide and/or propylene oxide with alcohols having a straight or branched alkyl chain, having from 6 to 22 carbon atoms, wherein the degree of alkoxylation (ethoxylation and/or propoxylation) is from 1 to 15, alternatively from 5 to 12. Such suitable nonionic surfactants are commercially available from Shell, for instance, under the trade name Neodol® or from BASF under the trade name Lutensol®.

The compositions of the present invention may comprise an anionic surfactant or a mixture thereof. The compositions of the present invention may comprise up to 15% by weight of the total composition of an anionic surfactant or a mixture thereof, alternatively from 0.1% to 15%, alternatively from 1% to 10%, even alternatively from 1% to 5%, and alternatively from 1% to 3%.

Anionic surfactants may be included herein as they contribute to the cleaning benefits of the hard-surface cleaning compositions of the present invention. Indeed, the presence of an anionic surfactant contributes to the greasy soap scum cleaning of the compositions herein. More generally, the presence of an anionic surfactant in the liquid acidic compositions of the present invention allows to lower the surface tension and to improve the wettability of the surfaces being treated with the liquid acidic compositions of the present invention. Furthermore, the anionic surfactant or a mixture thereof, helps to solubilize the soils in the compositions of the present invention.

Suitable anionic surfactants for use herein are all those commonly known by those skilled in the art. In one embodiment, the anionic surfactants for use herein include alkyl sulphonates, alkyl aryl sulphonates, or mixtures thereof.

Suitable linear alkyl sulphonates include C8 sulphonate like Witconate® NAS 8 commercially available from Witco.

Other anionic surfactants useful herein include salts (including, for example, sodium, potassium, ammonium, and substituted ammonium salts such as mono-, di- and triethanolamine salts) of soap, alkyl sulphates, alkyl aryl sulphates alkyl alkoxylated sulphates, C8-C24 olefinsulfonates, sulphonated polycarboxylic acids prepared by sulphonation of the pyrolyzed product of alkaline earth metal citrates, e.g., as described in British patent specification No. 1,082,179; alkyl ester sulfonates such as C14-16 methyl ester sulfonates; acyl glycerol sulfonates, alkyl phosphates, isethionates such as the acyl isethionates, N-acyl taurates, alkyl succinamates, acyl sarcosinates, sulfates of alkylpolysaccharides such as the sulfates of alkylpolyglucoside (the nonionic nonsulfated compounds being described below), alkyl polyethoxy carboxylates such as those of the formula RO(CH2CH2O) kCH2COO-M+ wherein R is a C8-C22 alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

E. Surface-Modifying Polymer

The compositions of the present invention may optionally comprise a vinylpyrrolidone homopolymer or copolymer, or a mixture thereof. Typically, the compositions of the present invention may comprise from 0.01% to 5% by weight of the total composition, of a vinylpyrrolidone homopolymer or copolymer, or a mixture thereof, alternatively from 0.05% to 3%, alternatively from 0.05% to 1%.

Suitable vinylpyrrolidone homopolymers for use herein are homopolymers of N-vinylpyrrolidone having the following repeating monomer:

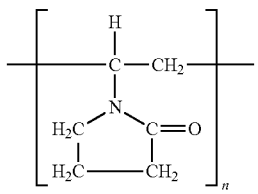

wherein n (degree of polymerisation) is an integer of from 10 to 1,000,000, alternatively from 20 to 100,000, and alternatively from 20 to 10,000.

Accordingly, suitable vinylpyrrolidone homopolymers ("PVP") for use herein have an average molecular weight of from 1,000 to 100,000,000, alternatively from 2,000 to 10,000,000, alternatively from 5,000 to 1,000,000, and alternatively from 50,000 to 500,000.

Suitable vinylpyrrolidone homopolymers are commercially available from ISP Corporation, New York, N.Y. and Montreal, Canada under the product names PVP K-15® (viscosity molecular weight of 10,000), PVP K-30® (average molecular weight of 40,000), PVP K-60® (average molecular weight of 160,000), and PVP K-90® (average molecular weight of 360,000). Other suitable vinylpyrrolidone homopolymers which are commercially available from BASF Cooperation include Sokalan HP 165®, Sokalan HP 12®, Luviskol K30®, Luviskol K60®, Luviskol K80®, Luviskol K90®; vinylpyrrolidone homopolymers known to persons skilled in the detergent field (see for example EP-A-262,897 and EP-A-256,696).

Suitable copolymers of vinylpyrrolidone for use herein include copolymers of N-vinylpyrrolidone and alkylenically unsaturated monomers or mixtures thereof.

The alkylenically unsaturated monomers of the copolymers herein include unsaturated dicarboxylic acids such as maleic acid, chloromaleic acid, fumaric acid, itaconic acid, citraconic acid, phenylmaleic acid, aconitic acid, acrylic acid, N-vinylimidazole and vinyl acetate. Any of the anhydrides of the unsaturated acids may be employed, for example acrylate, methacrylate. Aromatic monomers like styrene, sulphonated styrene, alpha-methyl styrene, vinyl toluene, t-butyl styrene and similar well known monomers may be used.

For example, suitable N-vinylimidazole N-vinylpyrrolidone polymers for use herein have an average molecular weight range from 5,000 to 1,000,000, alternatively from 5,000 to 500,000, alternatively from 10,000 to 200,000. The average molecular weight range was determined by light scattering as described in Barth H. G. and Mays J. W. Chemical Analysis Vol 113, "Modern Methods of Polymer Characterization".

Such copolymers of N-vinylpyrrolidone and alkylenically unsaturated monomers like PVP/vinyl acetate copolymers are commercially available under the trade name Luviskol® series from BASF.

In one execution of the present invention, vinylpyrrolidone homopolymers are selected.

The compositions of the present invention may optionally comprise a polysaccharide polymer or a mixture thereof. Typically, the compositions of the present invention may comprise from 0.01% to 5%, by weight of the total composition, of a polysaccharide polymer or a mixture thereof, alternatively from 0.05% to 3%, alternatively from 0.05% to 1%.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum or derivatives thereof, or mixtures thereof.

In one embodiment, the compositions of the present invention comprise a polysaccharide polymer selected from the group consisting of: carboxymethylcellulose, ethyl cellulose, hydroxyethyl cellulose, hydroxypropyl cellulose, hydroxymethyl cellulose, succinoglycan gum, Xanthan gum, gellan gum, guar gum, locust bean gum, tragacanth gum, derivatives of the aforementioned, and mixtures thereof. Alternatively, the compositions herein comprise a polysaccharide polymer selected from the group consisting of: succinoglycan gum, Xanthan gum, gellan gum, guar gum, locust bean gum, tragacanth gum, derivatives of the aforementioned, and mixtures thereof. Alternatively, the compositions herein comprise a polysaccharide polymer selected from the group consisting of: Xanthan gum, gellan gum, guar gum, derivatives of the aforementioned, and mixtures thereof. Alternatively, the compositions herein comprise Xanthan gum, derivatives thereof, or mixtures thereof.

Particularly polysaccharide polymers for use herein are Xanthan gum and derivatives thereof. Xanthan gum and derivatives thereof may be commercially available for instance from CP Kelco under the trade name Keltrol RD®, Kelzan S® or Kelzan T®. Other suitable Xanthan gums are commercially available by Rhodia under the trade name Rhodopol T® and Rhodigel X747®. Succinoglycan gum for use herein is commercially available by Rhodia under the trade name Rheozan®.

It has surprisingly been found that the polysaccharide polymers or mixtures thereof herein act as surface modifying polymers (alternatively combined with a vinylpyrrolidone homopolymer or copolymer, as described herein) and/or as thickening agents. Indeed, the polysaccharide polymers or mixtures thereof herein can be used to thicken the compositions of the present invention. It has been surprisingly found that the use of polysaccharide polymers or mixtures thereof herein, and alternatively Xanthan gum, provides excellent thickening performance to the compositions herein. Moreover, it has been found that the use of polysaccharide polymers or mixtures thereof herein, and alternatively Xanthan gum, provides excellent thickening whilst not or only marginally reducing the limescale removal performance. Indeed, thickened compositions usually tend to show a drop in soil/stain removal performance (which in turn requires an increased level of actives to compensate for the performance drop) due to the thickening. It has been found that this is due to the fact that the actives providing the soil/stain removal performance are less free to migrate to the soil/stain. However, it has been surprisingly found that when polysaccharide polymers or mixtures thereof herein, and alternatively Xanthan gum, are used as thickeners for the compositions herein, the drop in soil/stain removal performance is substantially reduced or even prevented.

Furthermore, without intending to be bound by theory, it has been shown that vinylpyrrolidone homopolymers or copolymers, alternatively the vinylpyrrolidone homopolymer, and polysaccharide polymers, alternatively Xanthan gum or derivatives thereof, described herein, when added into an aqueous acidic composition deliver improved shine to the treated surface as well as improved next-time cleaning benefit on said surface, while delivering good first-time hard-surface cleaning performance and good limescale removal performance. Furthermore, the formation of watermarks and/or limescale deposits upon drying is reduced or even eliminated.

Moreover, the vinylpyrrolidone homopolymers or copolymers and polysaccharide polymers further provide long lasting protection against formation of watermarks and/or deposition of limescale deposits, hence, long lasting shiny surfaces.

An additional advantage related to the use of the vinylpyrrolidone homopolymers or copolymers and polysaccharide polymers, in the acidic compositions herein, is that as they adhere on hard surface making them more hydrophilic, the surfaces themselves become smoother (this can be perceived by touching said surfaces) and this contributes to convey perception of surface perfectly descaled.

These benefits may be obtained at low levels of vinylpyrrolidone homopolymers or copolymers and polysaccharide polymers, alternatively Xanthan gum or derivatives thereof, described herein.

The compositions herein may further comprise a surface-modifying polymer other than the vinylpyrrolidone homo- or copolymers and polysaccharide polymers described herein above.

The composition herein may comprise up to 5%, alternatively of from 0.0001% to 3%, alternatively from 0.001% to 2%, and alternatively of from 0.01% to 1%, by weight of the total composition of said other surface-modifying polymers.

Other surface-modifying polymers may be optional ingredients herein as they deposit onto the surfaces cleaned with a composition of the present invention. Thereby, soil adherence, soap scum, limescale and/or mineral encrustation build-up, is prevented.

Suitable other surface-modifying polymers may be selected from the group consisting of: zwitterionic surface modification copolymers consisting of carboxylate- and permanent cationic-moieties; zwitterionic surface modifying polysulphobetaine copolymers; zwitterionic surface modifying polybetaine copolymers; silicone glycol polymers; and mixtures thereof.

Zwitterionic surface modification copolymers consisting of carboxylate- and permanent cationic-moieties, zwitterionic surface modifying polysulphobetaine copolymers and zwitterionic surface modifying polybetaine copolymers are described in WO 2004/083354, EP-A-1196523 and EP-A-1196527. Suitable zwitterionic surface modification copolymers consisting of carboxylate- and permanent cationic-moieties, zwitterionic surface modifying polysulphobetaine copolymers and zwitterionic surface modifying polybetaine copolymers are commercially available from Rhodia in the Mirapol SURF S-polymer series.

Alternative surface modification copolymers are described in the Applicant's co-pending European Patent Applications 07 113 156.9, these copolymers are sulphobetaine/vinyl-pyrrolidone and its derivatives copolymers. A particularly suitable sulphobetaine/vinyl-pyrrolidone and its derivatives copolymer is a copolymer of 90% moles of vinyl pyrrolidone and 10% moles of SPE (sulphopropyl dimethyl ammonium ethyl methacrylate) such as exemplified in Example 1.1 of the Applicant's co-pending European Patent Applications 07 113 156.9.

Suitable silicone glycols are described in the Applicant's co-pending European Patent Applications 03 447 099.7 and 03 447 098.9, in the section titled "Silicone glycol".

Silicone glycol polymers are commercially available from General electric, Dow Corning, and Witco (see European Patent Applications 03 447 099.7 and 03 447 098.9 for an extensive list of trade names of silicone glycol polymers).

In one embodiment of the present invention, the silicone glycol polymer herein is a Silicones-Polyethers copolymer, commercially available under the trade name SF 1288® from Momentive Performance Materials.

F. Radical Scavenger

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Radical scavengers for use herein may include di-tert-butyl hydroxy toluene (BHT), hydroquinone, di-tert-butyl hydroquinone, mono-tert-butyl hydroquinone, tert-butyl-hydroxy anysole, benzoic acid, toluic acid, catechol, t-butyl catechol, benzylamine, 1,1,3-tris(2-methyl-4-hydroxy-5-t-butylphenyl)butane, n-propyl-gallate or mixtures thereof, and di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and alternatively from 0.001% to 0.5% by weight. The presence of radical scavengers may contribute to the chemical stability of the compositions of the present invention.

G. Solvent

The compositions of the present invention may further comprise a solvent or a mixture thereof, as an optional ingredient. Solvents to be used herein include all those known to those skilled in the art of hard-surfaces cleaner compositions. In one embodiment, the compositions herein comprise an alkoxylated glycol ether (such as n-Butoxy Propoxy Propanol (n-BPP)) or a mixture thereof.

Typically, the compositions of the present invention may comprise from 0.1% to 5% by weight of the total composition, n of a solvent or mixtures thereof, alternatively from 0.5% to 5% by weight of the total composition and alternatively from 1% to 3% by weight of the total composition.

H. Additional Surfactant

The compositions of the present invention may comprise an additional surfactant, or mixtures thereof, on top of the nonionic surfactant and/or anionic surfactant already described herein. Additional surfactants may be desired herein as they further contribute to the cleaning performance and/or shine benefit of the compositions of the present invention. Surfactants to be used herein include cationic surfactants, amphoteric surfactants, zwitterionic surfactants, and mixtures thereof.

Accordingly, the compositions of the present invention may comprise up to 15% by weight of the total composition of another surfactant or a mixture thereof, on top of the nonionic surfactant already described herein, alternatively from 0.5% to 5%, even alternatively from 0.5% to 3%, and alternatively from 0.5% to 2%. Different surfactants may be used in the present invention including anionic, cationic, zwitterionic or amphoteric surfactants. It is also possible to use mixtures of such surfactants without departing from the spirit of the present invention.

Suitable surfactants for use herein are zwitterionic surfactants since they provide excellent grease soap scum cleaning ability to the compositions of the present invention.

Suitable zwitterionic surfactants for use herein contain both basic and acidic groups which form an inner salt giving both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used.

Some common examples of zwitterionic surfactants (i.e. betaine/sulphobetaine) are described in U.S. Pat. Nos. 2,082, 275, 2,702,279 and 2,255,082. For example Coconut dimethyl betaine is commercially available from Seppic under the trade name of Amonyl 265®. Lauryl betaine is commercially available from Albright & Wilson under the trade name Empigen BB/L®. A further example of betaine is Lauryl-imminodipropionate commercially available from Rhodia under the trade name Mirataine H2C-HA®.

In one embodiment, the composition comprises sulfobetaine surfactants as they may deliver optimum soap scum cleaning benefits. Examples of suitable sulfobetaine surfactants include tallow bis(hydroxyethyl) sulphobetaine, cocoamido propyl hydroxy sulphobetaines which are commercially available from Rhodia and Witco, under the trade name of Mirataine CBS® and Rewoteric AM CAS 15® respectively.

Amphoteric and ampholytic detergents which can be either cationic or anionic depending upon the pH of the system are represented by detergents such as dodecylbeta-alanine, N-alkyltaurines such as the one prepared by reacting dodecylamine with sodium isethionate of the teaching of U.S. Pat. No. 2,658,072, N-higher alkylaspartic acids such as those produced of the teaching of U.S. Pat. No. 2,438,091, and the products sold under the trade name "Miranol", and described in U.S. Pat. No. 2,528,378. Additional synthetic detergents and listings of their commercial sources can be found in McCutcheon's Detergents and Emulsifiers, North American Ed. 1980.

Suitable amphoteric surfactants include the amine oxides. Examples of amine oxides for use herein are for instance coconut dimethyl amine oxides, C12-C16 dimethyl amine oxides. Said amine oxides may be commercially available from Clariant, Stepan, and AKZO (under the trade name Aromox®). Other suitable amphoteric surfactants for the purpose of the invention are the phosphine or sulfoxide surfactants.

Cationic surfactants suitable for use in compositions of the present invention are those having a long-chain hydrocarbyl group. Examples of such cationic surfactants include the quaternary ammonium surfactants such as alkyldimethylammonium halogenides. Other cationic surfactants useful herein are also described in U.S. Pat. No. 4,228,044, Cambre, issued Oct. 14, 1980.

I. Dye

The compositions of the present invention may be colored. Accordingly, they may comprise a dye or a mixture thereof. Suitable dyes for use herein are acid-stable dyes. By "acid-stable", it is meant herein a compound which is chemically and physically stable in the acidic environment of the compositions herein.

J. Malodor Control Component

The hard surface cleaning composition comprises a malodor control component. The malodor control component may include at least one volatile aldehyde and an acid catalyst. The malodor control component is designed to deliver genuine malodor neutralization and not function merely by covering up or masking odors. A genuine malodor neutralization provides a sensory and analytically measurable (e.g. gas chromatograph) malodor reduction. Thus, if the malodor control component delivers a genuine malodor neutralization, the composition will reduce malodors in the vapor and/or liquid phase.

1. Volatile Aldehydes

The malodor control component includes a mixture of volatile aldehydes that neutralize malodors in vapor and/or liquid phase via chemical reactions. Such volatile aldehydes are also called reactive aldehydes (RA). Volatile aldehydes may react with amine-based odors, following the path of Schiff-base formation. Volatiles aldehydes may also react with sulfur-based odors, forming thiol acetals, hemi thiolacetals, and thiol esters in vapor and/or liquid phase. It may be desirable for these vapor and/or liquid phase volatile aldehydes to have virtually no negative impact on the desired perfume character of a product. Aldehydes that are partially volatile may be considered a volatile aldehyde as used herein.

Suitable volatile aldehydes may have a vapor pressure (VP) in the range of about 0.0001 torr to 100 torr, alternatively about 0.0001 torr to about 10 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The volatile aldehydes may also have a certain boiling point (B.P.) and octanol/water partition coefficient (P). The boiling point referred to herein is measured under normal standard pressure of 760 mmHg. The boiling points of many volatile aldehydes, at standard 760 mm Hg are given in, for example, "Perfume and Flavor Chemicals (Aroma Chemicals)," written and published by Steffen Arctander, 1969.

The octanol/water partition coefficient of a volatile aldehyde is the ratio between its equilibrium concentrations in octanol and in water. The partition coefficients of the volatile aldehydes used in the malodor control component may be more conveniently given in the form of their logarithm to the base 10, logP. The logP values of many volatile aldehydes have been reported. See, e.g., the Pomona92 database, available from Daylight Chemical Information Systems, Inc. (Daylight CIS), Irvine, Calif. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each volatile aldehyde, and takes into account the numbers and types of atoms, the atom connectivity, and chemical bonding. The ClogP values, which are the most reliable and widely used estimates for this physicochemical property, are alternatively used instead of the experimental logP values in the selection of volatile aldehydes for the malodor control component.

The ClogP values may be defined by four groups and the volatile aldehydes may be selected from one or more of these groups. The first group comprises volatile aldehydes that have a B.P. of about 250° C. or less and ClogP of about 3 or less. The second group comprises volatile aldehydes that have a B.P. of 250° C. or less and ClogP of 3.0 or more. The third group comprises volatile aldehydes that have a B.P. of 250° C. or more and ClogP of 3.0 or less. The fourth group comprises volatile aldehydes that have a B.P. of 250° C. or more and ClogP of 3.0 or more. The malodor control component may comprise any combination of volatile aldehydes from one or more of the ClogP groups.

In some embodiments, the malodor control component of the present invention may comprise, by total weight of the malodor control component, from about 0% to about 30% of volatile aldehydes from group 1, alternatively about 25%; and/or about 0% to about 10% of volatile aldehydes from group 2, alternatively about 10%; and/or from about 10% to about 30% of volatile aldehydes from group 3, alternatively about 30%; and/or from about 35% to about 60% of volatile aldehydes from group 4, alternatively about 35%.

Exemplary volatile aldehydes which may be used in a malodor control component include, but are not limited to, Adoxal (2,6,10-Trimethyl-9-undecenal), Bourgeonal (4-t-butylbenzenepropionaldehyde), Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3-cyclohexen-1-carbaldehyde), Florhydral (3-(3-Isopropyl-phenyl)-butyraldehyde), Citronellal (3,7-dimethyl 6-octenal), Cymal, cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), Helional (alpha-methyl-3,4-(methylenedioxy)-hydrocinnamaldehyde, hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupical, tricyclodecylidenebutanal (4-Tricyclo5210-2,6decylidene-8butanal), Melafleur (1,2,3,4,5,6,7,8-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undecadien-1-al), Citronellyl oxyacetaldehyde, Muguet aldehyde 50 (3,7-dimethyl-6-octenyl)oxyacetaldehyde), phenylacetaldehyde, Mefranal (3-methyl-5-phenyl pentanal), Triplal, Vertocitral dimethyl tetrahydrobenzene aldehyde (2,4-dimethyl-3-cyclohexene-1-carboxaldehyde), 2-phenylproprionaldehyde, Hydrotropaldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1-cyclohexene-1-carboxaldehyde).

Still other exemplary aldehydes include, but are not limited to, acetaldehyde (ethanal), pentanal, valeraldehyde, amylaldehyde, Scentenal (octahydro-5-methoxy-4,7-Methano-1H-indene-2-carboxaldehyde), propionaldehyde (propanal), Cyclocitral, beta-cyclocitral, (2,6,6-trimethyl-1-cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7-dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Lauric aldehyde, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2-isopropyl-5-methyl-2-hexenal, Trifernal, beta methyl Benzenepropanal, 2,6,6-Trimethyl-1-cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anisaldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3-phenylpropenoic aldehyde, Vanillin (4-methoxy 3-hydroxy benzaldehyde), Ethyl vanillin (3-ethoxy 4-hydroxybenzaldehyde), Hexyl Cinnamic aldehyde, Jasmonal H (alpha-n-hexyl-cinnamaldehyde), Floralozone, (para-ethyl-alpha,alpha-dimethyl Hydrocinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2-hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4-hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4 (1-methylethenyl)-1-cyclohexene-1-carboxaldehyde), 2,4-Dimethyl-3-cyclohexene carboxaldehyde, 2-Methyl-2-pentenal, 2-methylpentenal, pyruvaldehyde, formyl Tricyclodecan, Mandarin aldehyde, Cyclemax, Pino acetaldehyde, Corps Iris, Maceal, and Corps 4322.

In one embodiment, the malodor control component includes a mixture of two or more volatile aldehydes selected from the group consisting of 2-ethoxy Benzylaldehyde, 2-isopropyl-5-methyl-2-hexenal, 5-methyl Furfural, 5-methyl-thiophene-carboxaldehyde, Adoxal, p-anisaldehyde, Benzylaldehyde, Bourgenal, Cinnamic aldehyde, Cymal, Decyl aldehyde, Floral super, Florhydral, Helional, Lauric aldehyde, Ligustral, Lyral, Melonal, o-anisaldehyde, Pino acetaldehyde, P.T. Bucinal, Thiophene carboxaldehyde, trans-4-Decenal, trans trans 2,4-Nonadienal, Undecyl aldehyde, and mixtures thereof.

In some embodiments, the malodor control component includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes.

In one embodiment, the malodor control component includes a mixture of the volatile aldehydes listed in Table 1 and referred to herein as Accord A.

TABLE 1

| | Accord A | | | |
|---|---|---|---|---|
| Material | Wt. % | CAS Number | ClogP Group | VP (torr) @25° C. |
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the malodor control component includes a mixture of the volatile aldehydes listed in Table 2 and referred to herein as Accord B.

TABLE 2

Accord B

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the malodor control component includes a mixture of about 71.2% volatile aldehydes, the remainder being other an ester and an alcohol perfume raw material. This mixture is listed in Table 3 and referred to herein as Accord C.

TABLE 3

Accord C

| Material | Wt. % | CAS Number | ClogP Group | VP (torr) @25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| Flor Acetate | 11.800 | 5413-60-5 | 1 | 0.060 |
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with other perfume raw materials in an amount, for example, of about 10% by weight of the malodor control component. Additionally, the individual volatile aldehydes or a various combination of the volatile aldehydes can be formulated into a malodor control component. In certain embodiments, the volatile aldehydes may be present in an amount up to 100%, by weight of the malodor control component, alternatively from 1% to about 100%, alternatively from about 2% to about 100%, alternatively from about 3% to about 100%, alternatively about 50% to about 100%, alternatively about 70% to about 100%, alternatively about 80% to about 100%, alternatively from about 1% to about 20%, alternatively from about 1% to about 10%, alternatively from about 1% to about 5%, alternatively from about 1% to about 3%, alternatively from about 2% to about 20%, alternatively from about 3% to about 20%, alternatively from about 4% to about 20%, alternatively from about 5% to about 20%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control component of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control component contains an acid catalyst and contacts a sulfur-based malodor, the volatile aldehyde reacts with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, measured at 25° C., alternatively about 0.001 torr to about 14 torr, alternatively from about 0.001 to about 1, alternatively from about 0.001 to about 0.020, alternatively about 0.005 to about 0.020, alternatively about 0.010 to about 0.020.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalyst include those listed in Table 4.

TABLE 4

| Material | VP (torr) @ 25° C. |
|---|---|
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

Depending on the desired use of the malodor control component, one may consider the scent character or the affect on the scent of the malodor control component when selecting an acid catalyst. In some embodiments of the malodor control component, it may be desirable to select an acid catalyst that provides a neutral to pleasant scent. Such acid catalysts may have a VP of about 0.001 torr to about 0.020 torr, measured at 25° C., alternatively about 0.005 torr to about 0.020 torr, alternatively about 0.010 torr to about 0.020 torr Non-limiting examples of such acid catalyst include 5-methyl thiophene carboxaldehyde with carboxylic acid impurity, succinic acid, or benzoic acid.

The malodor control component may include about 0.05% to about 5%, alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst by weight of the malodor control component.

In an acetic acid system, the present malodor control component may include about 0.4% of acetic acid (50:50 TC:DPM, 0.4% acetic acid).

TABLE 5

| Sample Formulated | Actual % acetic acid in DPM | % Butanethiol reduction @ 30 min. |
|---|---|---|
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde (or RA), the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control component may have a pH from about 3 to about 8, alternatively from about 4 to about 7, alternatively from about, alternatively from about 4 to about 6.

3. Optional Ingredients

The malodor control component may, optionally, include odor masking agents, odor blocking agents, and/or diluents. For example, the malodor control component may include a mixture of volatile aldehydes for neutralizing a malodor, perfume ionones, and a diluent. Alternatively, the malodor control component may include 100% volatile aldehydes.

"Odor-masking agents" refer to known compounds (e.g. perfume raw materials) that mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds.

"Odor blocking agents" refer to known compounds that dull the human sense of smell.

Exemplary diluents include dipropylene glycol methyl ether, and 3-methoxy-3-methyl-1-butanol, and mixtures thereof.

The malodor control component may also, optionally, include perfume raw materials that solely provide a hedonic benefit (i.e. that do not neutralize malodors yet provide a pleasant fragrance). Suitable perfumes are disclosed in U.S. Pat. No. 6,248,135, which is incorporated in its entirety by reference.

II. Method of Cleaning a Hard-Surface or an Object

The present invention further encompasses a method of cleaning a hard surface or an object, alternatively removing limescale from said hard-surface or said object.

The method of the present invention comprises the steps of: applying a liquid acidic hard surface cleaning composition comprising formic acid, citric acid and an alkaline material, and having a pH of above 2.0; and mixtures thereof, onto said hard-surface or said object; leaving said composition on said hard-surface or said object to act; optionally wiping said hard-surface or object and/or providing mechanical agitation, and then rinsing said hard-surface or said object.

By "hard-surface", it is meant herein any kind of surfaces typically found in and around houses like bathrooms, kitchens, basements and garages, e.g., floors, walls, tiles, windows, sinks, showers, shower plastified curtains, wash basins, WCs, dishes, fixtures and fittings and the like made of different materials like ceramic, enamel, painted and un-painted concrete, plaster, bricks, vinyl, no-wax vinyl, linoleum, melamine, Formica®, glass, any plastics, metals, chromed surface and the like. The term surfaces as used herein also include household appliances including, but not limited to, washing machines, automatic dryers, refrigerators, freezers, ovens, microwave ovens, dishwashers and so on. Some hard surfaces cleaned with the liquid aqueous acidic hard surface cleaning composition herein are those located in a bathroom, in a toilet or in a kitchen, basements, garages as well as outdoor such as garden furniture, gardening equipments, driveways etc.

The objects herein are objects that are subjected to limescale formation thereon. Such objects may be water-taps or parts thereof, water-valves, metal objects, objects made of stainless-steel, cutlery and the like.

One method of cleaning a hard-surface or an object (alternatively removing limescale from said hard-surface or said object) comprises the step of applying a composition of the present invention onto said hard-surface or object, leaving said composition on said hard-surface or object to act, alternatively for an effective amount of time, alternatively for a period comprised between 1 and 10 minutes, alternatively for a period comprised between 2 and 4 minutes; optionally wiping said hard-surface or object with an appropriate instrument, e.g. a sponge; and then alternatively rinsing said surface with water.

Even though said hard-surface or object may optionally be wiped and/or agitated during the process herein, it has been surprisingly found that the process of the present invention allows good limescale removal performance without any additional mechanical wiping and/or agitation action. The lack of need for additional wiping and/or mechanical; agitation provides an added convenience for the user of the compositions herein.

In another execution of the present invention is provided a method of cleaning an object, alternatively removing limescale from an object, comprising the step of immersing said object in a bath comprising a composition of the present invention, leaving said object in said bath for the composition to act, alternatively for an effective amount of time, alternatively for a period comprised between 1 and 10 minutes, alternatively for a period comprised between 2 and 4 minutes; and then alternatively rinsing said object with water.

The compositions of the present invention may be contacted to the surface or the object to be treated in its neat form or in its diluted form. Alternatively, the composition is applied in its neat form.

By "diluted form", it is meant herein that said composition is diluted by the user, typically with water. The composition is diluted prior use to a typical dilution level of 10 to 400 times its weight of water, alternatively from 10 to 200 and alternatively from 10 to 100. Usual recommended dilution level is a 1.2% dilution of the composition in water.

The compositions of the present invention are particularly suitable for treating hard-surfaces located in and around the house, such as in bathrooms, toilets, garages, on driveways, basements, gardens, kitchens, etc., and alternatively in bathrooms. It is however known that such surfaces (especially bathroom surfaces) may be soiled by the so-called "limescale-containing soils". By "limescale-containing soils" it is meant herein any soil which contains not only limescale mineral deposits, such as calcium and/or magnesium carbonate, but also soap scum (e.g., calcium stearate) and other grease (e.g. body grease). By "limescale deposits" it is mean herein any pure limescale soil, i.e., any soil or stains composed essentially of mineral deposits, such as calcium and/or magnesium carbonate.

The compositions herein may be packaged in any suitable container, such as bottles, alternatively plastic bottles, optionally equipped with an electrical or manual trigger spray-head.

EXAMPLES

The examples herein are meant to exemplify the present invention but are not necessarily used to limit or otherwise define the scope of the present invention. All numerical values in the below examples are weight %, by total weight of the composition unless otherwise stated.

| | Examples: | | | | | | | | |
|---|---|---|---|---|---|---|---|---|---|
| | I | II | III | IV | V | VI | VII | VIII | IX |
| Acids | | | | | | | | | |
| Formic acid | 3.0 | 1.5 | 2.5 | 2.0 | 1.8 | 2.5 | 3.0 | 1.0 | 3.0 |
| Citric acid | 1.5 | 6.0 | 4.5 | 4.0 | 7.0 | 2.0 | 1.0 | 4.0 | 2.0 |
| Alkaline Material: | | | | | | | | | |
| NaOH - to pH: | 2.1 | 2.4 | 2.2 | | | | | 3.8 | 3.0 |
| KOH - to pH: | | | | 2.4 | 2.9 | 2.2 | 2.8 | | |
| Water | | | | up to 100% | | | | | |

| | Examples: | | | | | | | | |
|---|---|---|---|---|---|---|---|---|---|
| | X | XI | XII | XIII | XIV | XV | XVI | XVII | XVIII |
| Acids | | | | | | | | | |
| Formic acid | 2.0 | 2.7 | 2.5 | 1.8 | 1.5 | 2.0 | 2.8 | 1.8 | 4.0 |
| Acetic acid | — | — | 0.75 | — | 0.5 | — | — | — | — |
| Citric acid | 3.5 | 4.6 | 4.0 | 8.0 | 1.5 | 3.0 | 2.0 | — | — |
| Lactic acid | — | — | — | 1.0 | — | 2.0 | 1.0 | — | 1.5 |
| Sulfuric acid | — | — | — | — | — | — | — | 3.0 | 3.0 |
| Surfactants | | | | | | | | | |
| Neodol 91-8 ® | 0.5 | 2.2 | 2.2 | 2.2 | 2.5 | 0.45 | 2.5 | — | — |
| Sulphated Safol 23 ® | 2.0 | — | — | — | — | — | — | — | — |
| H-LAS | — | — | — | — | — | 0.80 | — | 0.90 | 1.30 |
| NaCS | — | — | — | — | — | 1.80 | — | 2.20 | 2.50 |
| Polymers: | | | | | | | | | |
| Kelzan T ® | 0.40 | 0.25 | 0.25 | 0.25 | 0.30 | 0.10 | 0.40 | 0.45 | 0.60 |
| PVP | 0.25 | 0.05 | — | 0.25 | 0.05 | — | 0.25 | — | — |
| SF 1288 ® | — | — | — | — | — | 0.60 | — | 0.90 | 1.80 |
| Solvent: | | | | | | | | | |
| n-BPP | 1.0 | — | — | 1.5 | — | — | — | — | — |
| Misc.: | | | | | | | | | |
| BHT | 0.03 | 0.03 | 0.03 | 0.03 | 0.05 | — | 0.03 | 0.15 | 0.15 |
| Malodor Control Component | 0.05 | 0.50 | 0.20 | 0.50 | 0.30 | 0.50 | 0.25 | 0.40 | 0.35 |
| Dye | 0.01 | 0.005 | 0.005 | 0.01 | 0.01 | 0.01 | 0.01 | 0.01 | 0.005 |
| Alkaline Material: | | | | | | | | | |
| KOH - to pH: | 2.3 | — | — | — | 2.8 | — | — | — | — |
| NaOH - to pH: | — | 2.2 | 2.3 | 3.6 | — | 2.5 | 2.3 | — | — |
| pH (w/o alkaline material added) | — | — | — | — | — | — | — | 0.5 | 0.5 |
| Water: | | | | up to 100% | | | | | |

| | Examples: | | | | |
|---|---|---|---|---|---|
| | XIX | XX | XXI | XXII | XXIII |
| Acids | | | | | |
| Formic acid | | 2.5 | 2.8 | 2.7 | 1.0 | 2.0 |
| Citric acid | | 3.6 | 1.0 | 2.0 | 3.0 | 1.0 |
| Oxalic acid | | 1.0 | — | — | — | — |

-continued

| Surfactants | | | | | |
|---|---|---|---|---|---|
| Neodol 91-8 ® | 2.5 | 0.5 | 2.2 | 1.5 | 2.0 |
| Sulphated Safol 23 ® | — | — | — | — | 0.8 |
| Sodium Lauryl Sulphate | — | 3.0 | 2.0 | 1.5 | — |
| Kelzan T ® | 0.28 | 0.10 | 0.35 | 0.25 | 0.40 |
| PVP | 0.05 | — | 0.25 | 0.05 | 0.25 |
| n-BPP | — | 3.5 | 2.5 | 1.6 | 2.5 |
| BHT | 0.04 | — | — | — | — |
| Malodor Control Component | 0.25 | 0.60 | 0.40 | 0.20 | 0.35 |
| Dye | 0.005 | 0.005 | 0.01 | 0.005 | 0.01 |
| KOH - to pH: | — | 3.6 | — | — | — |
| NaOH - to pH: | 2.3 | — | 3.0 | 3.3 | 3.6 |
| pH (w/o alkaline material added) | — | — | — | — | — |
| Water: | up to 100% | | | | |

Formic acid, citric acid, lactic acid, acetic acid, oxalic acid and sulphuric acid are commercially available from Aldrich.
Neodol 91-8 ® is a $C_9$-$C_{11}$ EO8 nonionic surfactant, commercially available from SHELL.
Sulphated Safol 23 ® is a branched $C_{12-13}$ sulphate surfactant based on Safol 23 ®, an alcohol commercially available from Sasol, which has been sulphated.
Sodium lauryl sulfate is a linear C12-14 sulfate which is commercially available from Aldrich.
n-BPP is n-butoxy propoxy propanol.
Kelzan T ® is a Xanthan gum supplied by Kelco.
PVP is a vinylpyrrolidone homopolymer, commercially available from ISP Corporation.
SF 1288 ® is a silicone-polyether copolymer, commercially available from Momentive Performance Materials.
BHT is Butylated Hydroxy Toluene Analytical Test—Effect of Volatile Aldehydes on Amine-Based and Sulfur-Based Malodors Malodor standards are prepared by pipeting 1 mL of butylamine (amine-based malodor) and butanethiol (sulfur-based malodor) into a 1.2 liter gas sampling bag. The bag is then filled to volume with nitrogen and allowed to sit for at least 12 hours to equilibrate.

A 1 μL sample of each volatile aldehyde listed in Table 6 and of each Accord (A, B, and C) listed in Tables 1 to 3 is pipeted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample +malodor standard are held at room temperature for 30 minutes. Then, a 1 mL headspace syringe is then used to inject 250 μL of each sample/malodor into a GC/MS split/splitless inlet. For amine analysis, a 1 mL headspace syringe is used to inject 500 μL of each sample/malodor immediately into the GC/MS split/splitless inlet. A GC pillow is used for the amine analysis to shorten the run times.

Samples are then analyzed using a GC/MS with a DB-5, 20 m, 1 μm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 6 shows the effect of certain volatile aldehydes on neutralizing amine-based and sulfur based malodors at 40 seconds and 30 minutes, respectively.

TABLE 6

| Perfume Raw Material (R—CHO) | At least 20% butylamine reduction at 40 secs.? | At least 20% butanethiol reduction at 30 mins.? |
|---|---|---|
| 2,4,5 Trimethoxy Benzaldehyde | No | No |
| 2,4,6-Trimethoxy-benzylaldehyde | No | No |
| 2-ethoxy benzylaldehyde | Yes | Yes |
| 2-isopropyl-5-methyl-2-hexenal | Yes | Yes |
| 2-methyl-3-(2-furyl)-propenal | No | No |
| 3,4,5 Trimethoxy Benzaldehyde | No | No |
| 3,4-Trimethoxy-benzylaldehyde | No | No |
| 4-tertbutyl benzylaldehyde | Yes | No |
| 5-methyl furfural | Yes | Yes |
| 5-methyl-thiophene-carboxaldehyde | No | Yes |
| Adoxal | Yes | No |
| Amyl cinnamic aldehyde | No | No |
| Benzylaldehyde | Yes | No |
| Bourgenal | No | Yes |
| Cinnamic aldehyde | Yes | Yes |
| Citronelyl Oxyacetaldehyde | No | No |
| Cymal | Yes | No |
| Decyl aldehyde | Yes | No |
| Floral Super | Yes | Yes |
| Florhydral | Yes | Yes |
| Floralozone | No | No |
| Helional | Yes | No |
| Hydroxycitronellal | No | No |
| Lauric aldehyde | Yes | No |
| Ligustral | Yes | No |
| Lyral | Yes | No |
| Melonal | Yes | No |
| Methyl nonyl acetaldehyde | No | No |
| o-anisaldehyde | Yes | Yes |
| p-anisaldehyde | Yes | No |
| Pino acetaldehyde | Yes | Yes |
| P.T. Bucinal | Yes | No |
| Thiophene Carboxaldehyde | Yes | No |
| Trans-4-decenal | Yes | Yes |
| Trans Trans 2,4-Nonadienal | Yes | No |
| Undecyl aldehyde | Yes | No |

Table 7 shows the percent reduction of butylamine and butaniethiol at 40 seconds and 30 minutes, respectively, for Accords A, B, and C.

TABLE 7

| Accord | % reduction of butylamine at 40 secs. | % reduction of butanethiol at 30 mins. |
|---|---|---|
| Accord A | 76.58 | 25.22 |
| Accord B | 51.54 | 35.38 |
| Accord C | 65.34 | 24.98 |

Analytical Test—Effect of Acid Catalysts on Sulfur-Based Malodors

The above analytical test is repeated using samples containing an acid catalyst to test their effect on sulfur-based malodors. Specifically, a 1 µL aliquot of each of the following controls and acid catalyst samples are pipeted into individual 10 mL silanized headspace vials in duplicate: thiophene carboxyaldehyde as a control; a 50/50 mixture of thiophene carboxaldehyde and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

FIG. 1 demonstrates that low vapor pressure acid catalysts provide up to 3 times better reduction of sulfur-based malodors in comparison to the control.

Analytical Test—Effect of Volatile Aldehydes and Acid Catalyst on Amine-Based and Sulfur-Based Malodors The above analytical test is repeated using sample formulations containing volatile aldehydes (or RA) and an acid catalyst, as outlined in Tables 8 and 9.

Tables 8 and 9 show that a perfume mixture having as little as 1% volatile aldehyde along with 1.5% acid catalyst performs better at reducing butylamine and butanethiol than the same perfume mixture having 5% volatile aldehyde.

TABLE 8

| Formulation | % butylamine reduction at 40 secs. | | % butanethiol reduction at 30 mins. | |
|---|---|---|---|---|
| Perfume Mixture w/ 5% RA (Control) | 34.21 | — | 2.40 | — |
| Perfume Mixture w/ 1% RA and w/ 1.5% Benzoic Acid | 41.63 | +7.42 | 11.95 | +9.55 |
| Perfume Mixture w/ 3% RA and w/ 1.5% Benzoic Acid | 36.19 | +1.98 | 13.56 | +11.16 |
| Perfume A Mixture w/ 5% RA and w/ 1.5% Benzoic Acid | 41.26 | +7.05 | 9.56 | +5.02 |

TABLE 9

| Formulation | % butylamine Reduction at 40 secs. | | % butanethiol reduction at 30 mins. | |
|---|---|---|---|---|
| Perfume mixture w/ 5% RA (Control) | 4.94 | — | 10.52 | — |
| Perfume mixture w/ 1% RA and w/ 1.5% Benzoic Acid | 11.61 | +6.67 | 18.82 | +8.30 |
| Perfume mixture w/ 3% RA and w/ 1.5% Benzoic Acid | 26.89 | +21.95 | 14.85 | +4.33 |
| Perfume mixture w/ 5% RA and w/ 1.5% Benzoic Acid | 20.27 | +15.33 | 16.84 | +6.32 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A hard surface cleaning composition comprising:
   (a) an acidic component;
   (b) a surfactant selected from the group consisting of nonionic surfactants, anionic surfactants, cationic surfactants; amphoteric surfactants, zwitterionic surfactants, and mixtures thereof; and
   (c) a surface modifying polymer;
   (d) a malodor control component comprising an effective amount of:
      (i) at least one volatile aldehyde; and
      (ii) 5-methyl thiophene carboxylic acid; and
   (e) an aqueous carrier.

2. The composition of claim 1 wherein said at least one volatile aldehyde is selected from the group consisting of 2-ethoxy benzylaldehyde, 2-isopropyl-5-methyl-2-hexenal, 5-methyl furfural, cinnamic aldehyde, floral super, florhydral, o-anisaldehyde, pino acetaldehyde, trans-4-decenal, and mixtures thereof.

3. The composition of claim 1 wherein said at least one volatile aldehyde comprise flor super and o-anisaldehyde.

4. The composition of claim 1 wherein said at least one volatile aldehyde have a vapor pressure from about 0.001 torr to about 0.100 torr.

5. The composition of claim 1 wherein said at least one volatile aldehyde comprise about 25% of group 1 volatile aldehydes, by weight of said malodor control component.

6. The composition of claim 1 wherein said at least one volatile aldehyde comprise about 10% of group 2 volatile aldehydes, by weight of said malodor control component.

7. The composition of claim 1 wherein said at least one volatile aldehyde comprise from about 10% to about 30% of group 3 volatile aldehydes, by weight of said malodor control component.

8. The composition of claim 1 wherein said at least one volatile aldehyde comprise from about 35% to about 60% of group 4 volatile aldehydes, by weight of said malodor control component.

9. The composition of claim 1 wherein said at least one volatile aldehyde is selected from the group consisting of: Accord A, Accord B, Accord C, and mixtures thereof.

10. The composition of claim 1 wherein said at least one volatile aldehyde comprise about 1% to about 10% of Accord A, by weight of said malodor control component.

11. The composition of claim 1 wherein said composition has a pH of above about 2.

12. The composition of claim 1 wherein said at least one volatile aldehyde comprise three or more volatile aldehydes having a VP of about 0.001 torr to about 0.100 torr.

13. The composition of claim 1 wherein said at least one volatile aldehyde are present in an amount from about 0.015% to about 1%, by weight of said hard surface cleaning composition.

14. The composition of claim 1 wherein said acidic component is about 0.01% to about 5%, by weight of the total composition, of formic acid.

15. The composition of claim 1, wherein said acidic component is from about 0.1 to about 12%, by weight of the total composition, of citric acid.

16. The composition of claim 1, wherein said acidic component comprises formic acid and citric acid.

17. The composition of claim 1, wherein said surfactant is a nonionic surfactant which is the condensation product of ethylene and/or propylene oxide with an alcohol having a straight alkyl chain comprising from about 6 to about 22 carbon atoms, wherein the degree of ethoxylation/propoxylation is from about 1 to about 15.

18. The composition of claim 1, wherein said surfactant is an alkyl sulphate anionic surfactant.

19. The composition of claim 1, wherein said surfactant is a mixture of a nonionic surfactant and an anionic surfactant.

20. The composition of claim 1, wherein said surface modifying polymer is selected from the group consisting of: vinylpyrrolidone homopolymer or copolymer; polysaccharide polymer; and mixtures thereof.

21. The composition of claim 1 further comprising a material selected from the group consisting of: solvents, radical scavengers, caustics, perfumes, dyes, and mixtures thereof.

22. The composition of claim 1, wherein said composition further comprises an alkaline material selected from the group consisting of: sodium hydroxide, potassium hydroxide, lithium hydroxide, alkali metal, monoethanolamine, triethanolamine, ammonia, ammonium carbonate, choline base, and mixtures thereof.

23. The composition of claim 1, wherein said composition further comprises and alkaline material selected from the group consisting of: sodium hydroxide, potassium hydroxide, and mixtures thereof.

24. The composition of claim 1, wherein said composition further comprises uncomplexed cyclodextrin.

25. The composition of claim 1 wherein said composition further comprises a water-soluble metallic salt selected from the group consisting of: zinc salts, copper salts, and mixtures thereof.

26. A method of cleaning a hard surface or an object, comprising the steps of:
(a) applying the hard surface cleaning composition of claim 1 onto said hard-surface or said object;
(b) leaving said composition on said hard-surface or said object to act; optionally, wiping said hard-surface or object; and
(c) rinsing said hard-surface or said object.

* * * * *